US012620457B2

(12) United States Patent
Sun et al.

(10) Patent No.: US 12,620,457 B2
(45) Date of Patent: May 5, 2026

(54) RETROSYNTHESIS USING NEURAL NETWORKS

(71) Applicant: Google LLC, Mountain View, CA (US)

(72) Inventors: Ruoxi Sun, Mountain View, CA (US); Li Li, Sunnyvale, CA (US); Bo Dai, San Jose, CA (US); Hanjun Dai, Atlanta, GA (US)

(73) Assignee: Google LLC, Mountain View, CA (US)

( * ) Notice: Subject to any disclaimer, the term of this patent is extended or adjusted under 35 U.S.C. 154(b) by 698 days.

(21) Appl. No.: 18/009,835

(22) PCT Filed: Jun. 28, 2021

(86) PCT No.: PCT/US2021/039416
§ 371 (c)(1),
(2) Date: Dec. 12, 2022

(87) PCT Pub. No.: WO2021/263238
PCT Pub. Date: Dec. 30, 2021

(65) Prior Publication Data
US 2023/0223112 A1 Jul. 13, 2023

Related U.S. Application Data

(60) Provisional application No. 63/044,991, filed on Jun. 26, 2020.

(51) Int. Cl.
*G16C 20/10* (2019.01)
*G06N 3/0455* (2023.01)
*G16C 20/70* (2019.01)

(52) U.S. Cl.
CPC ........... *G16C 20/10* (2019.02); *G06N 3/0455* (2023.01); *G16C 20/70* (2019.02)

(58) Field of Classification Search
CPC ....... G16C 20/10; G16C 20/70; G06N 3/0455
See application file for complete search history.

(56) References Cited

U.S. PATENT DOCUMENTS

| | | | | |
|---|---|---|---|---|
| 10,586,162 B2 * | 3/2020 | Beymore | ................. | G06N 7/01 |
| 10,915,818 B1 * | 2/2021 | Patel | ....................... | G06N 3/044 |
| 11,315,019 B2 * | 4/2022 | Nachum | .................. | G06N 3/09 |
| 11,354,582 B1 * | 6/2022 | Prat | ......................... | G06V 30/10 |

(Continued)

OTHER PUBLICATIONS

Bahdanau et al., "Neural Machine Translation by Jointly Learning to Align and Translate," arXiv, May 19, 2016, 15 pages.

(Continued)

*Primary Examiner* — Mohammed H Zuberi
(74) *Attorney, Agent, or Firm* — Fish & Richardson P.C.

(57) ABSTRACT

Methods, systems, and apparatus, including computer programs encoded on computer storage media, for performing retrosynthesis using a neural network. One of the methods includes generating a prediction of a set of a plurality of predicted reactants that are combinable to generate a target compound, the generating comprising processing, for each of a plurality of candidate sets of reactants, a network input characterizing the candidate set using a neural network, determining, for each candidate set of the plurality of candidate sets, a score using the generated probabilities; and selecting a particular candidate set of one or more reactants using the determined scores.

20 Claims, 5 Drawing Sheets

400

Process a network input using a first subnetwork to generate a predicted prior probability of the candidate set of reactants — 402

Process the network input using a second subnetwork to generate a predicted conditional probability of the target compound conditioned on the candidate set of reactants — 404

Process the network input using a third subnetwork to generate a predicted conditional probability of the candidate set of reactants conditioned on the target compound — 406

Determine, for each candidate set of reactants, a score using the generated probabilities — 408

Select a particular candidate set of reactants using the determined scores — 410

(56) References Cited

U.S. PATENT DOCUMENTS

| 11,676,685 | B2 * | 6/2023 | Jaganathan | G06N 3/0455 |
| | | | | 706/25 |
| 11,900,225 | B2 * | 2/2024 | Oono | G06N 3/082 |
| 12,360,511 | B2 * | 7/2025 | Hong | G05B 19/4155 |
| 2003/0028330 | A1 * | 2/2003 | Cheng | G16C 20/30 |
| | | | | 702/30 |
| 2006/0031027 | A1 * | 2/2006 | Alman | G16C 20/30 |
| | | | | 702/25 |
| 2018/0012124 | A1 * | 1/2018 | Hara | G16C 99/00 |
| 2020/0027528 | A1 * | 1/2020 | Coley | G16C 20/70 |
| 2022/0189587 | A1 * | 6/2022 | Clevert | G16C 20/70 |
| 2022/0328141 | A1 * | 10/2022 | Gedeck | G06N 3/0464 |
| 2022/0351053 | A1 * | 11/2022 | Norvaisas | G06N 7/01 |
| 2022/0359043 | A1 * | 11/2022 | Stec | G16C 20/70 |
| 2022/0399085 | A1 * | 12/2022 | Bowden, Jr. | G06N 3/042 |
| 2022/0406417 | A1 * | 12/2022 | Kaneko | G06N 3/04 |
| 2023/0258081 | A1 * | 8/2023 | Jin | E21B 43/16 |
| | | | | 166/250.01 |
| 2023/0335231 | A1 * | 10/2023 | Abdallah | G06N 3/088 |
| 2024/0047014 | A1 * | 2/2024 | Yang | G16C 20/10 |
| 2024/0249801 | A1 * | 7/2024 | Wiltschko | G06N 3/04 |
| 2025/0087311 | A1 * | 3/2025 | Mukherjee | G06N 3/0895 |

OTHER PUBLICATIONS

Besag, "Statistical analysis of non-lattice data," Journal of the Royal Statistical Society: Series D (The Statistician), Sep. 1975, 24(3):179-195.

Cho et al., "Learning Phrase Representations using RNN Encoder-Decoder for Statistical Machine Translation," arXiv, Sep. 3, 2014, 15 pages.

Coley et al., "Computer-assisted retrosynthesis based on molecular similarity," ACS central science, Nov. 16, 2017, 3(12):1237-1245.

Coley et al., "Machine learning in computer-aided synthesis planning," Accounts of chemical research, May 2018, 51(5):1281-1289.

Corey, "Robert Robinson Lecture. Retrosynthetic thinking—essentials and examples," Chemical Society Reviews, 1988, 17:111-133.

Corey, "The Logic of Chemical Synthesis: Multistep Synthesis of Complex Carbogenic Molecules (Nobel Lecture)," Angewandte Chemie International Edition in English, May 1991, 30(5):455-465.

Dai et al., "Discriminative Embeddings of Latent Variable Models for Structured Data," Proceedings of The 33rd International Conference on Machine Learning, 2016, 10 pages.

Dai et al., "Retrosynthesis Prediction with Conditional Graph Logic Network," Neural Information Processing Systems, 2019, 11 pages.

Devlin et al., "BERT: Pre-training of Deep Bidirectional Transformers for Language Understanding," arXiv, May 24, 2019, 16 pages.

DiMasi et al., "Innovation in the pharmaceutical industry: New estimates of R&D costs," J. Health Econ., May 2016, 47:20-33.

Duvenaud et al., "Convolutional networks on graphs for learning molecular fingerprints," Advances in neural information processing systems, 2015, 9 pages.

Gilmer et al., "Neural message passing for quantum chemistry," Proceedings of the 34th International Conference on Machine Learning, 2017, 70:1263-1272.

github.com [online], "Rdkit: Open-source cheminformatics software," Sep. 4, 2016, retrieved on May 10, 2023, retrieved from URL<https://github.com/rdkit/rdkit/releases/tag/Release_2016_09_4>, 2 pages.

Hamilton et al., "Inductive representation learning on large graphs," Advances in neural information processing systems, Dec. 2017, pp. 1024-1034.

He et al., "Dual learning for machine translation," Advances in neural information processing systems, Dec. 2016, pp. 820-828.

Hinton, "A Practical Guide to Training Restricted Boltzmann Machines," Neural networks: Tricks of the trade, 2012, pp. 599-619.

International Preliminary Report on Patentability in International Appln. No. PCT/US2021/039416, mailed on Jan. 5, 2023, 8 pages.

International Search Report and Written Opinion in International Appln. No. PCT/US2021/039416, mailed on Oct. 21, 2021, 13 pages.

Karpov et al., "A transformer model for retrosynthesis," International Conference on Artificial Neural Networks, Sep. 9, 2019, pp. 817-830.

Kearnes et al., "Molecular graph convolutions: moving beyond fingerprints," Journal of computer-aided molecular design, Aug. 24, 2016, 30:595-608.

Kindermann et al., "Markov Random Fields and Their Applications," Contemporary Mathematics, 1980, 147 pages.

LeCun et al., "A tutorial on energy-based learning," Predicting structured data 1, 2006, 59 pages.

Li et al., "Gated Graph Sequence Neural Networks," arXiv, Sep. 22, 2017, 20 pages.

Liu et al., "Retrosynthetic Reaction Prediction Using Neural Sequence-to-Sequence Models," ACS central science, Sep. 5, 2017, 3:1103-1113.

Paul et al., "How to improve R&D productivity: the pharmaceutical industry's grand challenge," Nat. Rev. Drug Discov., Mar. 2010, 9:203-214.

Rogers et al., "Extended-connectivity fingerprints," Journal of chemical information and modeling, Apr. 28, 2010, 50:742-754.

Schwaller et al., "Molecular transformer: A model for uncertainty-calibrated chemical reaction prediction," ACS central science, Aug. 30, 2019, 5:1572-1583.

Segler et al., "Neural-Symbolic Machine Learning for Retrosynthesis and Reaction Prediction," Chemistry—A European Journal, Jan. 30, 2017, 23:5966-5971.

Shi et al., "A Graph to Graphs Framework for Retrosynthesis Prediction," arXiv, Aug. 20, 2021, 10 pages.

Sutskever et al., "Sequence to sequence learning with neural networks," Advances in neural information processing systems, Dec. 2014, pp. 3104-3112.

Szymkuc et al., "Computer-Assisted Synthetic Planning: The End of the Beginning," Angewandte Chemie International Edition, May 10, 2016, 55:5904-5937.

Tang et al., "Question Answering and Question Generation as Dual Tasks," arXiv, Aug. 4, 2017, 9 pages.

Vaswani et al., "Attention is All you Need," Advances in Neural Information Processing Systems, 2017, 11 pages.

Velickovic et al., "Graph Attention Networks," arXiv, Feb. 4, 2018, 12 pages.

Wang et al., "BERT has a Mouth, and It Must Speak: BERT as a Markov Random Field Language Model," arXiv, Apr. 9, 2019, 7 pages.

Wei et al., "Code Generation as a Dual Task of Code Summarization," Advances in Neural Information Processing Systems, Dec. 2019, pp. 6559-6569.

Weininger, "SMILES, a chemical language and information system. 1. Introduction to methodology and encoding rules," Journal of chemical information and computer sciences, Feb. 1988, 28:31-36.

Xia et al., "Dual supervised learning," Proceedings of the 34th International Conference on Machine Learning, 2017, 70:3789-3798.

Yang et al., "Xlnet: Generalized autoregressive pretraining for language understanding," Advances in neural information processing systems, 2019, pp. 5754-5764.

Zheng et al., "Predicting Retrosynthetic Reactions Using Self-Corrected Transformer Neural Networks," Journal of Chemical Information and Modeling, Jan. 27, 2020, 60:47-55.

* cited by examiner

350

TRAINING ENGINE 360

PRIOR
PROB. OF
REACTANTS
372

CONDITIONAL
PROB. OF TARGET
GIVEN REACTANTS
374

PARAM.
UPDATE
362

PARAM.
UPDATE
362

FIRST NEURAL
NETWORK 310

SECOND NEURAL
NETWORK 320

SAMPLED SET OF
REACTANTS 352

SAMPLED TARGET
COMPOUND 354

THIRD NEURAL
NETWORK 330

400

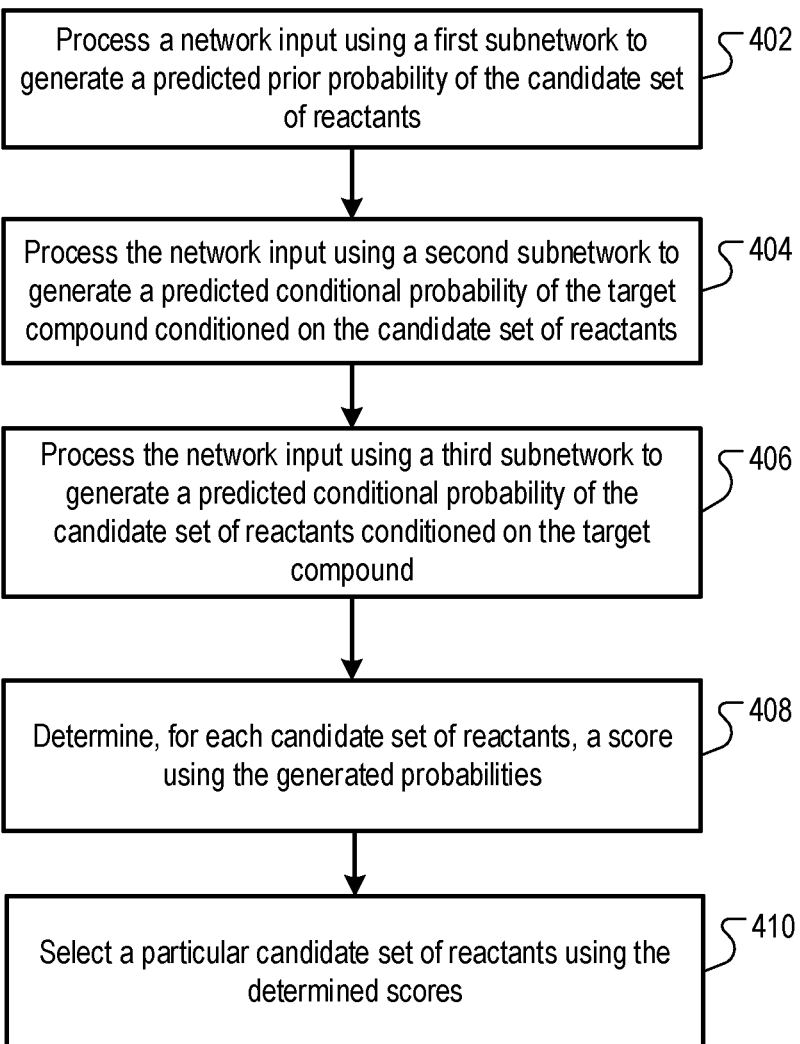

Process a network input using a first subnetwork to generate a predicted prior probability of the candidate set of reactants ⌐402

Process the network input using a second subnetwork to generate a predicted conditional probability of the target compound conditioned on the candidate set of reactants ⌐404

Process the network input using a third subnetwork to generate a predicted conditional probability of the candidate set of reactants conditioned on the target compound ⌐406

Determine, for each candidate set of reactants, a score using the generated probabilities ⌐408

Select a particular candidate set of reactants using the determined scores ⌐410

FIG. 4

RETROSYNTHESIS USING NEURAL NETWORKS

CROSS-REFERENCE TO RELATED APPLICATION

This application is a National Stage Application under 35 U.S.C. § 371 of International Application No. PCT/US2021/039416, filed on Jun. 28, 2021, which claims priority to U.S. Provisional Application Ser. No. 63/044,991, filed Jun. 26, 2020, the entirety of which are herein incorporated by reference.

BACKGROUND

This specification relates to neural networks.

Neural networks are machine learning models that employ one or more layers of nonlinear units to predict an output for a received input. Some neural networks include one or more hidden layers in addition to an output layer. The output of each hidden layer is used as input to one or more other layers in the network, i.e., one or more other hidden layers, the output layer, or both. Each layer of the network generates an output from a received input in accordance with current values of a respective set of parameters.

SUMMARY

This specification describes a system implemented as computer programs on one or more computers in one or more locations that performs retrosynthesis using a neural network. Retrosynthesis is the process of determining, from a target chemical compound, a set of chemical reactants for synthesizing the target compound.

In one aspect there is described a method for generating a prediction of a set of a plurality of predicted reactants that are combinable to generate a target compound. The generating comprises processing, for each of a plurality of candidate sets of reactants, a network input characterizing the candidate set using a neural network.

The processing comprises processing the network input using a first subnetwork to generate a predicted prior probability of the candidate set of reactants, in particular a prior probability according to a data distribution of sets of predicted reactants and target compounds. For example the prior probability may be a prior probability that the set of a plurality of predicted reactants is combinable to generate the target compound. The processing also comprises processing the network input using a second subnetwork to generate a predicted conditional probability of the target compound conditioned on the candidate set of reactants according to the (empirical) data distribution. The processing also comprises processing the network input using a third subnetwork to generate a predicted conditional probability of the candidate set of reactants conditioned on the target compound according to the (e.g. empirical) data distribution.

The method further comprises determining, for each candidate set of the plurality of candidate sets, a score using the generated probabilities, and selecting a particular candidate set of one or more reactants using the determined scores.

In some implementations the method performs one-step retrosynthesis but in such implementations multi-step retrosynthesis may be performed by applying the method recursively. That is, in some implementations the method generates a prediction of a set of a plurality of predicted reactants that are combinable in one-step without having first to make intermediate molecules, to generate the target compound.

The network input characterizing the candidate set of reactants may be e.g. any type of representation of the set of reactants. For example in some implementations the network input represents the set of reactants as a one-dimensional sequence of tokens e.g. each reactant may be represented as a string of characters. There are various standardized approaches for representing chemical structures in this way e.g. based around SMILES (simplified molecular-input line-entry system) or a variant thereof; or using other linear notations.

In implementations the method includes synthesizing the target compound, i.e. physically combining the particular candidate set of one or more reactants selected by the method to chemically synthesize, i.e. to physically generate, the target compound.

The above-described data distribution may be an empirical data distribution i.e. a data distribution that is determined by experimental data (from physical molecules) e.g. that has been learned during training.

The subject matter described in this specification can be implemented in particular embodiments so as to realize one or more of the following advantages.

Using techniques described in this specification, a system can automatically perform retrosynthesis in an efficient and accurate manner to determine an optimal set of reactants to use to synthesize a target compound. The search space of possible sets of reactants for synthesizing a particular target compound can be very large, growing exponentially with the number of individual reactants considered. For example, even when only considering 1000 unique reactants that can be included in a set of reactants to synthesize a target compound, the number of candidate sets that can be generated is on the order of $10^{300}$. A system can use the techniques described herein to drastically reduce the time and computational cost required to determine an optimal set of reactants.

Using techniques described in this specification, a training system can perform consistent training of a neural network to generate predicted probabilities that unify the forward direction of reaction prediction and the backward direction of retrosynthesis. That is, the training system can leverage the duality of the forward and backward directions to ensure that the neural network generates consistent predicted probabilities.

After training using the described dual loss, the neural network is able to generate predictions that are more accurate than some existing approaches such as some existing graph-based models for retrosynthesis. Furthermore, the neural network can use an autoregressive architecture for each subnetwork, which yields higher capacity and better performance than some existing models for retrosynthesis.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4 is a flow diagram of an example process for performing retrosynthesis using a neural network.

Like reference numbers and designations in the various drawings indicate like elements.

DETAILED DESCRIPTION

This specification describes a system that performs retrosynthesis using a neural network. This specification also describes a system that trains a neural network to perform retrosynthesis.

Figure 1:
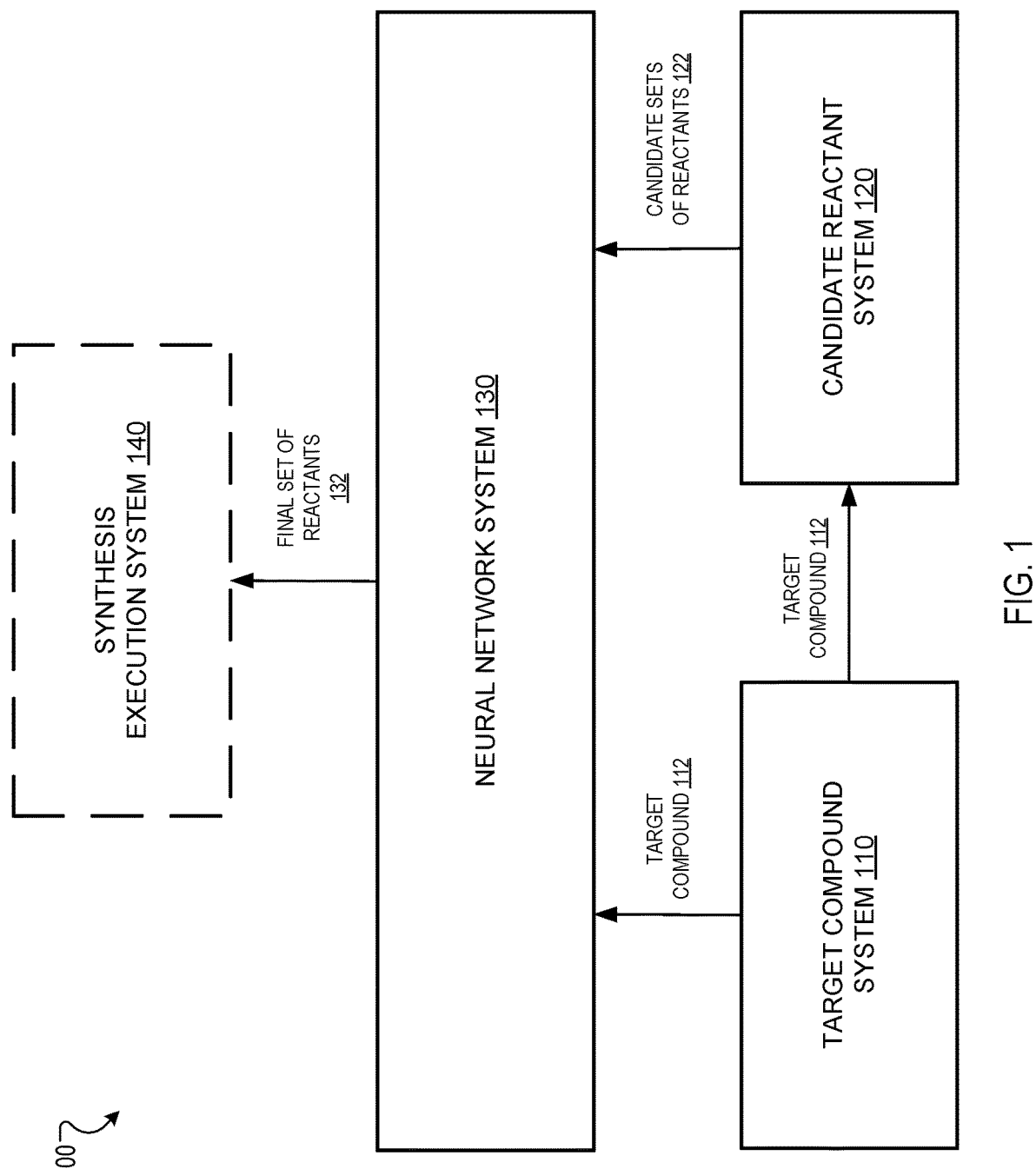
FIG. 1 is a diagram of an example retrosynthesis system.

FIG. 1 is a diagram of an example retrosynthesis system 100. The retrosynthesis system 100 is an example of a system implemented as computer programs on one or more computers in one or more locations, in which the systems, components, and techniques described below can be implemented.

The retrosynthesis system 100 includes a target compound system 110, a candidate reactant system 120, and a neural network system 130.

The target compound system 110 is configured to determine a target compound 112 to be retrosynthesized, i.e., a target compound 112 for which the retrosynthesis system 100 is to determine a set of reactants 132 that synthesizes the target compound 112.

In some implementations, the target compound system 110 obtains an input from an external system that identifies the target compound 112. For example, the target compound system 110 can obtain a user input from a user of the retrosynthesis system 100 that identifies the target compound 112 that the user wishes to be retrosynthesized. As a particular example, the target compound system 110 can obtain an input that includes the chemical formula and/or the name of the target compound 112. Some other examples of ways to represent a target compound 112 are discussed below.

As another example, the target compound system 110 can obtain an input from an external system that is configured to perform in silico screening of candidate target compounds to identify the target compound 112 that has one or more desired qualities. For example, the external system can be a simulation system that automatically simulates the interaction between the target compound 112 and other compounds.

As another example, the target compound system 110 can obtain an input from an external system that is configured to perform high-throughput screening (HTS) of many different candidate target compounds to identify the target compound 112 that has one or more desired qualities. For example, the external system can be a robotic system that includes one or more robots configured to perform screening, e.g., HTS.

In some other implementations, the target compound system 110 can determine the target compound 112 without receiving an external input. For example, the target compound system 110 can itself be an in silico screening system or an HTS system as described above.

After determining the target compound 112, the target compound system 110 can provide data characterizing the target compound 112 to the candidate reactant system 120.

The candidate reactant system 120 is configured to determine multiple different candidate sets 122 of reactants that may synthesize the target compound 112. Each candidate set 122 of reactants includes one or more reactants, where the candidate reactant system 120 has determined that it is possible or likely that the one or more reactants synthesize the target compound 112.

In some implementations, the candidate reactant system 120 determines one or more of the multiple different candidate sets 122 of reactants using templates that each identify, for target compounds exhibiting a respective pattern (called a "target pattern"), a corresponding pattern (called a "reactant pattern") for candidate sets 122 of reactants that are known to synthesize target compounds. In this specification, a "pattern" for a set of one or more compounds (e.g., the target compound 112 or the candidate set 122 of reactants) is data defining one or more characteristics that the compounds in the set share. For example, a pattern for a set of compounds can be defined by a network graph that includes multiple nodes (e.g., nodes representing molecules) and edges between pairs of nodes (e.g., edges representing chemical bonds between molecules). If a graph representation of a compound includes a subgraph that matches the pattern, then the compound is defined to "match" the pattern. In this example, a template can be defined by a graph rewriting rule that specifies how to transform the target pattern (i.e., the graph pattern corresponding to a target compound) to the reactant pattern (i.e., the graph pattern corresponding to a set of reactants). As another example, the template can be defined by a graph rewriting rule that specifies how to transform the reactant pattern to the target pattern.

The candidate reactant system 120 can maintain a database of templates. Given the target compound 112, the candidate reactant system 120 can identify one or more templates in the database for which the target compound 112 matches the target pattern of the template. Then, for each identified template, the candidate reactant system 120 can identify one or more candidate sets 122 of reactants that match the reactant pattern of the identified pattern.

Instead of or in addition to using templates, the candidate reactant system 120 can determine one or more of the multiple different candidate sets 122 of reactants using the neural network the neural network system 130. As described in more detail below, the neural network system 130 is configured to execute a neural network that processes a network input generated from the target compound 112 and a candidate set 122 of reactants and generates a network output characterizing a score that represents a likelihood that the candidate set 122 of reactants will synthesize the target compound 112. After the neural network has been trained, the candidate reactant system 120 can sample pairs of target compounds and sets of reactants that are likely to have a high score. Thus, given the target compound 112, the candidate reactant system 120 can use the trained neural network to sample corresponding candidate sets 122 of reactants that are likely to have a high score. Example techniques for sampling from the neural network are discussed in more detail below with reference to FIG. 3.

In some implementations, the candidate reactant system 120 can generate candidate sets 122 of reactants that include reactants that satisfy one or more conditions. For example, the candidate reactant system 120 can generate candidate sets 122 that include only reactants that are commercially available or that are themselves synthesizable using commercially available reactants. That is, if a particular reactant is not commercially available and cannot be easily synthesized, then it will not be useful for the system to output a set 132 of reactants that includes the particular reactant, as the set 132 cannot be practically used to synthesize the target compound 112.

As mentioned above, the neural network system 130 is configured to obtain a network input generated from (i) data identifying the target compound 112 and (ii) data identifying a particular candidate set 122 of reactants, and to process the network input using a neural network to generate a network output characterizing a score that represents a likelihood that the particular candidate set 122 of reactants will synthesize the target compound 112.

For example, the target compound 112 can be represented by a sequence of tokens, e.g., the simplified molecular input line entry system (SMILES) representation of the target compound 112. Similarly, the candidate set 122 of reactants can be represented by a sequence of tokens that includes a respective subsequence representing each reactant in the candidate set 122, e.g., the SMILES representation of the reactant in the candidate set 122. In this example, the neural network of the neural network system 130 can be configured to process (i) the sequence of tokens representing the target compound 112 and (ii) the sequence of tokens representing the candidate set 122 and to generate the score for the candidate set 122. As a particular example, the neural network can be a recurrent neural network. As another particular example, the neural network can be an attention-based neural network that attends across the tokens in the two sequences.

As another example, the target compound 112 and the candidate set 122 of reactants can be represented by respective graphs, as described above. In this example, the neural network of the neural network system 130 can be a graph neural network (GNN) that is configured to process (i) the graph representing the target compound 112 and (ii) the graph representing the candidate set 122 and to generate the score for the candidate set 122.

An example neural network that is configured to perform retrosynthesis is described in more detail below with reference to FIG. 2.

For each candidate set 122 generated by the candidate reactant system 120, the neural network system 130 can generate a respective score, as described above. The neural network system 130 can then select, using the generated scores, a final set 132 of reactants from the multiple different candidate sets 122 of reactants. For example, the neural network system 130 can select the candidate set 122 that corresponds to the highest score.

In some implementations, the neural network system 130 can update the scores generated by the neural network to generate a final score for each candidate set 122 of reactants. For example, the neural network system 130 can update the scores according to one or more constraints or preferences for the synthesis of the target compound 112.

As a particular example, the neural network system 130 can determine, for each candidate set 122 of reactants, a number of retrosynthesis steps required to synthesize the target compound 122 using the candidate set 122. The neural network system 130 can then update the scores for the candidate sets 122 to reward candidate sets 122 that have fewer retrosynthesis steps (i.e., lowering the score for candidate sets 122 that have relatively many retrosynthesis steps and raising the score for candidate sets 122 that have relatively few retrosynthesis steps), because generally a candidate set that requires fewer retrosynthesis steps is preferred. In some implementations, the neural network system 130 can determine to discard candidate sets 122 that have a number of retrosynthesis steps that exceeds a predetermined threshold (i.e., determine not to select any such candidate set 122 to be the final set 132 of reactants). Instead or in addition, the neural network system 130 can scale the scores according to the number of retrosynthesis steps, e.g., by multiplying the score for a candidate set 122 by the inverse of the number of retrosynthesis steps of the candidate set 122.

As another particular example, the neural network system 130 can determine, for each candidate set 122 of reactants, a selection of solvents and/or reagents that can be used to synthesize the target compound 112 using the candidate set 122 of reactants. The neural network system 130 can then update the scores for candidate sets 122 to reward candidate sets 122 that use preferred solvents and/or reagents. For instance, a user of the retrosynthesis system 100 might prefer not to use a particular solvent because it is hazardous or bad for the environment. In this example, the neural network system 130 can determine a lower final score for candidate sets 122 that require the particular solvent and a higher final score for candidate sets 122 that do not require the particular solvent to synthesize the target compound 112. In some implementations, the neural network system 130 can determine to discard candidate sets 122 that require "blacklisted" solvents and/or reactants, i.e., solvents and/or reactants that have been identified, e.g., by a user of the system 100, as disallowed.

As another particular example, the neural network system 130 can determine, for each candidate set 122 of reactants, a temperature at which the candidate set 122 of reactants can synthesize the target compound 112. The system can then update the scores for candidate sets 122 to reward candidate sets 122 that do not require extreme temperature to synthesize the target compound 112. In some implementations, the neural network system 130 can determine to discard candidate sets 122 that require temperatures that are outside of a predetermined acceptable range. Instead or in addition, the neural network system 130 can scale the score of a candidate set 122 according to the extent to which the required temperature of the candidate set 122 deviates from a predetermined range, e.g., by multiplying the score by the inverse of the difference between the required temperature and the closest temperature in the predetermined range.

After determining the final set 132 of reactants, the retrosynthesis system 100 can provide data identifying the final set 132 to a synthesis execution system 140. The synthesis execution system 140 can be configured to synthesize the reactants in the final set 132 to generate the target compound 112. For example, the synthesis execution system 140 can include one or more robotic components that can automatically execute the synthesis.

Instead or in addition to provide data identifying the final set 132 to a synthesis execution system 140, the retrosynthesis system 100 can provide data identifying the final set 132 to a user system for display to a user of the retrosynthesis system 100.

Figure 2:
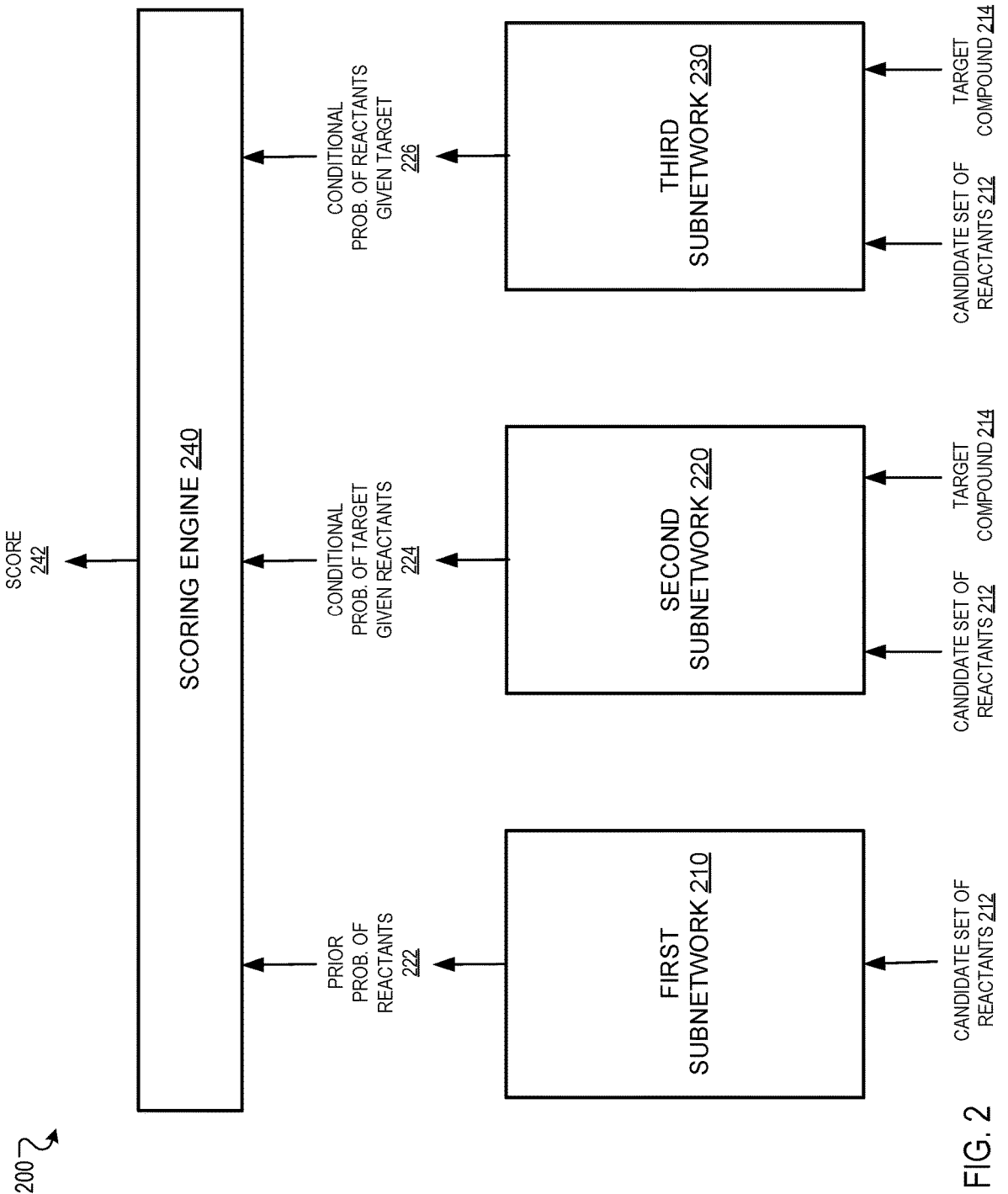
FIG. 2 is a diagram of an example neural network system configured to perform retrosynthesis.

FIG. 2 is a diagram of an example neural network system 200 configured to perform retrosynthesis. The neural network system 200 is an example of a system implemented as computer programs on one or more computers in one or more locations, in which the systems, components, and techniques described below can be implemented.

The neural network system 200 is configured to obtain data identifying (i) a target compound 214 and (ii) a candidate set 212 of reactants, and to process a network input generated from the obtained data to generate score 242 that represents a likelihood that the candidate set 212 of reactants can synthesize the target compound 214. For example, the neural network system 200 can be the neural network system 130 depicted in FIG. 1.

The neural network system 200 includes three subnetworks 210, 220, and 230, each of which are configured to generate a prediction for a different likelihood related to the candidate set 212 of reactants and the target compound 214.

The first subnetwork 210 is configured to process a first subnetwork input generated from the candidate set 212 of reactants and to generate a predicted prior probability 222 of the candidate set 212 of reactants. That is, the first subnetwork 210 is configured to generate a prior probability p(X) of the candidate set of reactants X, which is a prediction of the likelihood of the candidate set X according to a data distribution of sets of reactants, e.g., according to an empirical data distribution of sets of reactants determined from a training data set.

For example, the first subnetwork input can be a sequence of tokens that represents the candidate set 212, e.g., where the sequence includes a respective subsequence characterizing each reactant in the candidate set 212. The subsequence corresponding to a particular reactant can include tokens that collectively represent the particular reactant, e.g., where each token represents a component of the structure of the reactant such as an atom, bond, molecule, substructure or, potentially, stereochemistry. As a particular example, the subsequence can be the simplified molecular input line entry system (SMILES) representation of the reactant. As another example the subsequence can be a representation based on a SELFIES (SELF-referencIng Embedded Strings) representation of the reactant (arXiv:1905.13741).

In some implementations, the first subnetwork 210 is a self-attention based neural network that attends to the tokens of the sequence representing the candidate set 212. For example, the first subnetwork 210 can be a transformer neural network that includes an encoder configured to process, e.g., a placeholder input and to generate an encoder output, and a decoder configured to process (i) the encoder output and (ii) the sequence characterizing the candidate set 212 of reactants to generate the predicted prior probability p(X) 222 of the candidate set 212 of reactants. The placeholder input can be any choice of one or more tokens, e.g., period '.'. As another example, the first subnetwork 210 can include only the decoder of the transformer neural network that is configured to process the sequence characterizing the candidate set 212 of reactants to generate the predicted prior probability 222.

In particular, the decoder of the transformer neural network can be an autoregressive neural network that is configured to iteratively generate a next token in a sequence of tokens by processing the previously-generated tokens in the sequence of tokens. The output of the decoder can include, for each possible next token, a respective score characterizing a likelihood that the possible next token should be selected to be the next token in the sequence.

In this example, the decoder of the first subnetwork 210 can be configured to iteratively process the first k tokens in the sequence representing the candidate set 212 and to generate an output that identifies, for each possible token (e.g., each possible SMILES token), a likelihood that the possible token should be selected for the sequence. The first subnetwork 210 can then identify the likelihood corresponding to the $(k+1)^{th}$ token in the sequence representing the candidate set 212 (i.e., the actual next token in the sequence). In this way the first subnetwork 210 can determine a likelihood corresponding to each token in the sequence representing the candidate set 212 (conditioned on the previous tokens in the sequence). The first subnetwork 210 can then multiply the determined likelihoods together to generate the predicted prior probability p(X) 222 of the candidate set 212 of reactants, since the prior probability p(X) is equal to the product of the likelihood of each token of X conditioned on the previous tokens, i.e., $p(X)=p(x_0) \cdot p(x_1|x_0) \cdot p(x_2|x_0, x_1) \ldots$.

In some other implementations, the first subnetwork 210 can be a graph neural network that is configured to process a graphical representation of the candidate set 212 of reactants (e.g., graphical representation described above where each node of the graph represents a respective molecule and each edge represents a chemical bond between respective molecules) and to generate the predicted probability p(X) 222.

In some other implementations, the first subnetwork 210 can be a feedforward neural network that is configured to process an embedding of the candidate set 212 of reactants (e.g., the sequence of tokens described above or any other appropriate embedding) and to generate the predicted probability p(X) 222. In this specification, an embedding is an ordered collection of numeric values that represents an input in a particular embedding space. For example, an embedding can be a vector of floating point or other numeric values that has a fixed dimensionality.

The second subnetwork 220 is configured to process a second subnetwork input generated from the candidate set 212 of reactants and the target compound 214 and to generate a predicted conditional probability 224 of the target compound 214 given the candidate set 212 of reactants. That is, the second subnetwork 220 is configured to generate a predicted conditional probability p(y|X) of the target compound y conditioned on the candidate set of reactants X according to an empirical data distribution of pairs of (i) target compounds and (ii) sets of reactants.

For example, as described above the second subnetwork input can include (i) a sequence of tokens that represents the candidate set 212 and (ii) a sequence of tokens that represents the target compound 214.

In some implementations, the second subnetwork 220 is a self-attention based neural network that attends to the tokens of the sequences representing the candidate set 212 and the target compound 214. For example, the second subnetwork 220 can be a transformer neural network that includes an encoder configured to process the sequence characterizing the candidate set 212 of reactants and to generate an encoder output, and a decoder configured to process i) the encoder output and ii) the sequence characterizing the target compound 214 and to generate the predicted conditional probability p(y|X) 224 of the target compound 214 conditioned on the candidate set 212 of reactants.

In particular, the decoder of the second subnetwork 220 can be configured to iteratively process the first k tokens in the sequence representing the target compound 214 and to generate an output that identifies, for each possible token (e.g., each possible SMILES token), a likelihood that the possible token should be selected for the sequence. The second subnetwork 220 can then identify the likelihood corresponding to the (k+1)th token in the sequence representing the target compound 214 (i.e., the actual next token in the sequence). In this way the second subnetwork 220 can determine a likelihood corresponding to each token in the sequence representing the target compound 214 (conditioned on the previous tokens in the sequence). The second subnetwork 220 can then multiply the determined likelihoods together to generate the predicted conditional probability p(y|X) 224 of the target compound 214 conditioned on the candidate set 212 of reactants, since the conditional probability p(y|X) is equal to the product of the likelihood of each token of y conditioned on the previous tokens and X, i.e., $p(y|X)=p(y_0|X) \cdot p(y_1|y_0, X) \cdot p(y_2|y_1, y_0, X) \ldots$.

In some other implementations, the second subnetwork 220 is a graph neural network that is configured to process (i) a graphical representation of the candidate set 212 of reactants and (ii) a graphical representation of the target compound 214 and to generate the predicted probability p(y|X) 224.

In some other implementations, the second subnetwork 220 is a feedforward neural network that is configured to process (i) an embedding of the candidate set 212 of reactants and (ii) an embedding of the target compound 214 and to generate the predicted probability p(y|X) 224.

The third subnetwork 230 is configured to process a third subnetwork input generated from the candidate set 212 of reactants and the target compound 214 and to generate a predicted conditional probability 226 of the candidate set 212 of reactants given the target compound 214. That is, the third subnetwork 230 is configured to generate a predicted conditional probability p(X|y) of the candidate set of reactants X conditioned on the target compound y according to the empirical data distribution of pairs of (i) target compounds and (ii) sets of reactants.

For example, as described above the third subnetwork input can include (i) a sequence of tokens that represents the candidate set 212 and (ii) a sequence of tokens that represents the target compound 214.

In some implementations, the third subnetwork 230 is a self-attention based neural network that attends to the tokens of the sequences representing the candidate set 212 and the target compound 214. For example, the third subnetwork 230 can be a transformer neural network that includes an encoder configured to process the sequence characterizing the target compound 214 and to generate an encoder output, and a decoder configured to process (i) the encoder output and (ii) the sequence characterizing the candidate set 212 of reactants and to generate the predicted conditional probability p(X|y) 226 of the candidate set 212 of reactants conditioned on the target compound 214.

In particular, the decoder of the third subnetwork 230 can be configured to iteratively process the first k tokens in the sequence representing the candidate set 212 and to generate an output that identifies, for each possible token (e.g., each possible SMILES token), a likelihood that the possible token should be selected for the sequence. The third subnetwork 230 can then identify the likelihood corresponding to the $(k+1)^{th}$ token in the sequence representing the candidate set 212 (i.e., the actual next token in the sequence). In this way the third subnetwork 230 can determine a likelihood corresponding to each token in the sequence representing the candidate set 212 (conditioned on the previous tokens in the sequence). The third subnetwork 230 can then multiply the determined likelihoods together to generate the predicted conditional probability p(X|y) 226 of the candidate set 212 of reactants conditioned on the target compound 214, since the conditional probability p(X|y) is equal to the product of the likelihood of each token of X conditioned on the previous tokens and y, i.e., $p(X|y)=p(x_0|y) \cdot p(x_1|x_0, y) \cdot p(x_2|x_1, x_0, y) \ldots$.

In some other implementations, the third subnetwork 230 is a graph neural network that is configured to process i) a graphical representation of the candidate set 212 of reactants and ii) a graphical representation of the target compound 214 and to generate the predicted probability p(X|y) 226.

In some other implementations, the third subnetwork 230 is a feedforward neural network that is configured to process i) an embedding of the candidate set 212 of reactants and ii)

an embedding of the target compound 214 and to generate the predicted probability p(X|y) 226.

In implementations a self-attention based neural network as described above is a neural network with one or more self-attention layers i.e. a layer configured to apply a self-attention mechanism. The one or more self-attention layers may be also referred to as transformer neural network layers. A transformer neural network as described above may include an encoder coupled to a decoder, each of the encoder and decoder including one or more self-attention neural network layers.

In general a self-attention mechanism maps a query and a set of key-value pairs to an output, where the query, keys, and values are all vectors. The output is computed as a weighted sum of the values, where the weight assigned to each value is computed by a compatibility function of the query with the corresponding key. The exact self-attention mechanism applied depends on the configuration of the attention neural network. A self-attention mechanism is configured to relate different positions in the same sequence to determine a transformed version of the sequence as an output. For example a self-attention layer may generate a query and a key-value pair for an input e.g. derived from a sequence of tokens, and may then apply each of the queries to each of the key-value pairs, to determine a transformed version of the input. Tokens of a processed sequence may be combined with a position encoding value to define a position of a token in the sequence.

The neural network system 200 includes a scoring engine 240 that is configured to process (i) the prior probability 222 of the candidate set 212, (ii) the conditional probability 224 of the target compound 214 given the candidate set 212, and (iii) the conditional probability 226 of the candidate set 212 given the target compound 214, and to generate the score 242.

For example, the determined score can be dependent upon e.g. proportional to p(X) generated by the first subnetwork, p(y|X) generated by the second subnetwork, and p(X|y) generated by the third subnetwork. As a particular example, the score can be equal to or proportional to $\exp(\log p(X)+\log p(y|X)+\log p(X|y))$.

The neural network system 200 can be executed for each of multiple different candidate sets 212 of reactants, and the respective scores 242 for the different candidate sets 212 can be used to identify a final set of reactants that will be used to synthesize the target compound 214, as described above.

Figure 3A:
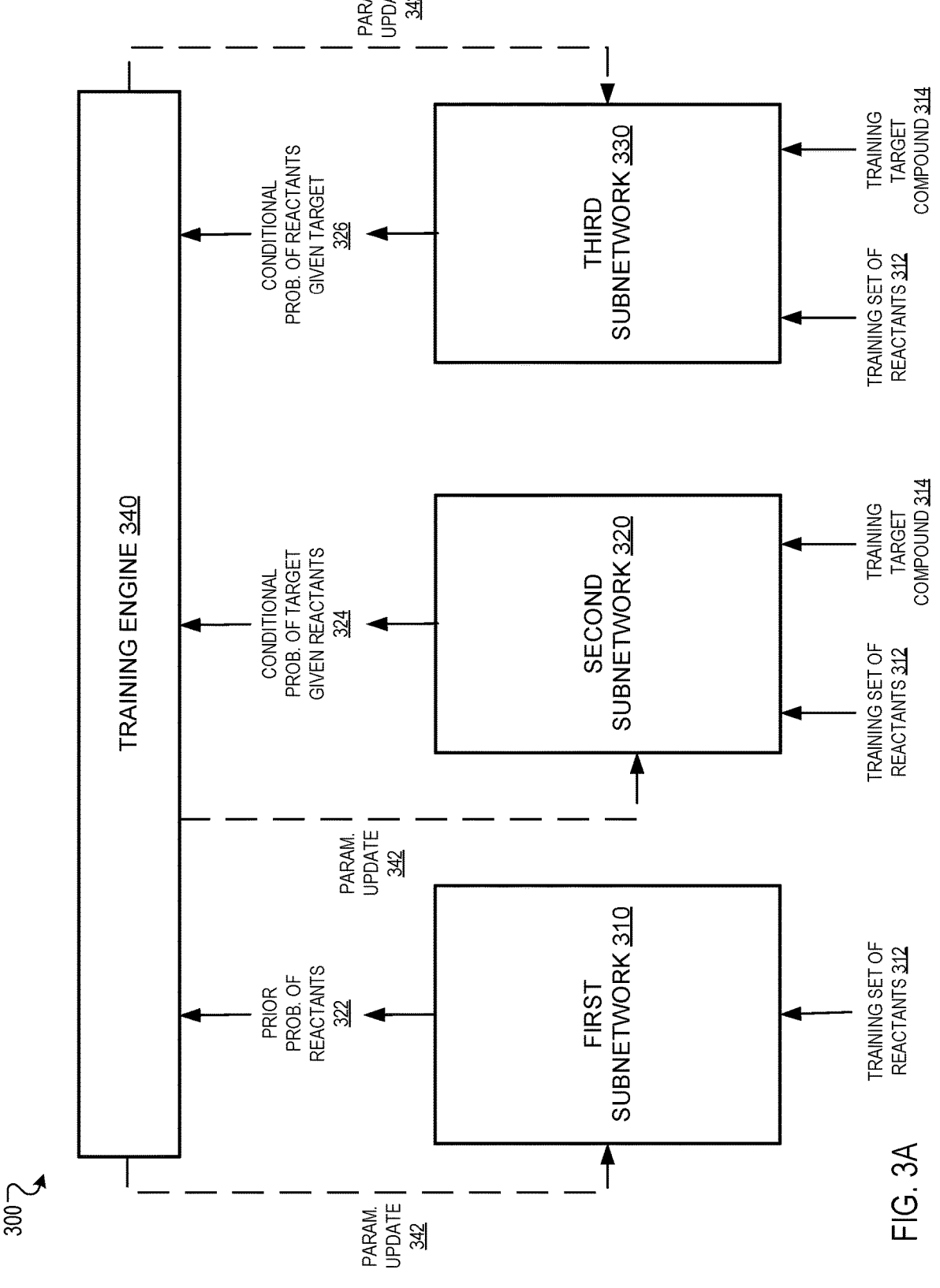
FIG. 3A and FIG. 3B are diagrams of example training systems configured to train a neural network to perform retrosynthesis.
Figure 3B:
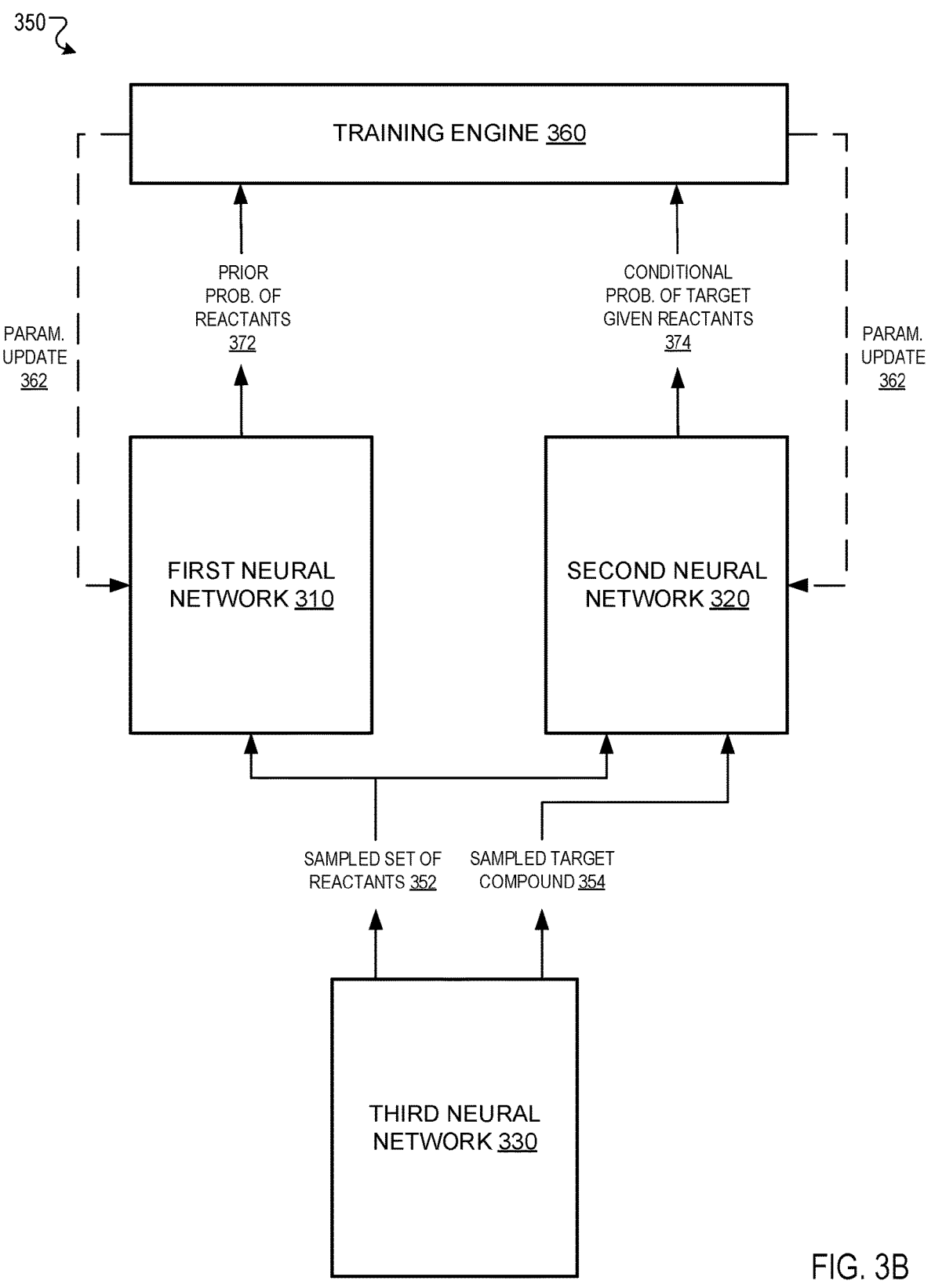

FIG. 3A and FIG. 3B are diagrams of example training systems 300 and 350, respectively, that are configured to train a neural network to perform retrosynthesis. The training systems 300 and 350 are examples of systems implemented as computer programs on one or more computers in one or more locations, in which the systems, components, and techniques described below can be implemented.

The neural network trained by the training systems 300 and 350 are configured to process a network input characterizing (i) a target compound and (ii) a candidate set of reactants and to generate a score for the candidate set, as described above. The neural network includes three subnetworks 310, 320, and 330, which can be configured similarly to the subnetworks 210, 220, and 230, respectively, described above with reference to FIG. 2. That is, the first subnetwork 310 can be configured to process a first subnetwork input characterizing the candidate set and to generate a prior probability p(X) of the candidate set; the second subnetwork 320 can be configured to process the second subnetwork input characterizing the target compound and the candidate set and to generate a conditional probability p(y|X) of the target compound given the candidate set; and the third subnetwork 330 can be configured to process a third subnetwork input characterizing the candidate set and the target compound and to generate a conditional probability p(X|y) of the candidate set given the target compound.

The training systems 300 and 350 can train the neural network using a dual loss function that leverages the fact that the joint probability p(X, y) can be factorized in two ways: a "forward" direction p(X)p(y|X) which represents synthesis given a set of reactants, and a "backward" direction p(y)p (X|y) which represents retrosynthesis given a target compound. In theory, the probabilities corresponding to both directions should be equal, i.e., equal to p(X, y). Thus, the dual loss can encourage the subnetworks 310, 320, and 330 of the neural network to generate probabilities that satisfy this equality. In some implementations, the p(y) value can be fixed, e.g., fixed at a value of one, because the target compound is predetermined.

Referring, to FIG. 3A, the training system 300 is configured to train the subnetworks 310, 320, and 330 of the neural network in parallel.

The training system 300 can obtain a training example that includes (i) a training set 312 of reactants and ii) a training target compound 314, and process the training example using the neural network to generate a first subnetwork output 322 corresponding to the first subnetwork 310 (characterizing the prior probability of the training set 312), a second subnetwork output 324 corresponding to the second subnetwork 320 (characterizing the conditional probability of the training target compound 314 given the training set 312), and a third subnetwork output corresponding to the third subnetwork 330 (characterizing the conditional probability of the training set 312 given the training target compound). A training engine 340 of the training system 300 can then determine an update 342 to the parameters of the neural network in order to minimize a dual loss that characterizes, for the training set of reactants, a difference between (i) a first predicted joint probability of the training set of reactants and the training target compound defined by the first subnetwork output and the second subnetwork output and (ii) a second predicted joint probability of the training set of reactants and the training target compound defined by the third subnetwork output.

As a particular example, the dual loss can penalize a KL divergence between (i) a distribution corresponding to the first predicted joint probability and (ii) a distribution corresponding to the second predicted joint probability. For instance, the dual loss can be equal to, proportional to, or generated from:

$$\sum_{(X,y)\in(\mathcal{X},\mathcal{y})} P(X, y) \log\left(\frac{P(X, y)}{Q(X, y)}\right)$$

where (X, y) is the training set of reactants and training target compound, ( $\mathcal{X}$, $\mathcal{y}$) is the training data set, P(X, y) is the first joint probability, and Q(X, y) is the second joint probability.

Optionally data augmentation may be used, permuting an order of the training set of reactants in a training sample, for order invariance.

In some implementations, instead of or in addition to penalizing the different between the respective likelihoods of the forward and backward directions, the dual loss can penalize the difference between (i) the one or both of the two distributions described above and (ii) the empirical distribution of the training data. As a particular example, the training system 300 can sample the training example from an empirical data distribution (e.g., a predetermined empirical data distribution defined by a training data set), and determine the loss according to the empirical data distribution. Thus in implementations the empirical data distribution is determined by the training data. The empirical data distribution can include, for each pair of (i) training target compound and (ii) training set of reactants, a corresponding joint probability. The dual loss can include a term $\hat{E}[\log p(X)+\log p(y|X)]$ corresponding to the first subnetwork output and the second subnetwork output, where $\hat{E}[\bullet]$ indicates an expectation over the empirical data distribution. The dual loss can include a term $\hat{E}[\log p(X|y)]$ corresponding to the third subnetwork output, where $\hat{E}[\bullet]$ indicates an expectation over the empirical data distribution. Example dual losses are discussed in more detail below with reference to FIG. 3B.

Referring to FIG. 3B, the training system 350 can train the third subnetwork 330 in a first training stage and the first subnetwork 310 and second subnetwork 320 in a second training phase.

In the first training phase, to train the third subnetwork 330, the training system 350 can sample training examples that each include a training target compound and a training set of reactants, and determine updates to the parameters of the third subnetwork 330 according to a difference between (i) a predicted joint probability determined using the third subnetwork output and (ii) the empirical data distribution of the training data, as described above with reference to FIG. 3A. For example, the training system 350 can determine parameter updates using backpropagation and gradient descent, e.g. by backpropagating gradients of the dual loss function.

In the second training phase, the training system 350 can use the third subnetwork 330 to sample training examples for the first subnetwork 310 and the second subnetwork 320. That is, the training system 350 can sample, from a predicted data distribution defined by the trained subnetwork, a training example that includes (i) a set 352 of reactants and ii) a target compound 354. For example, the training system 350 can sample the training example using beam search on the trained third subnetwork 330.

The training system 350 can then process a first subnetwork input generated from the sampled set 352 of reactants using the first subnetwork 310 to generate a first subnetwork output 372 characterizing predicted p(X), as described above. The training system 350 can process a second subnetwork input generated from the sampled set 352 and the sampled target compound 354 using the second subnetwork 320 to generate a second subnetwork output 374 characterizing predicted p(y|X), as described above.

A training engine 360 of the training system 350 can then determine the dual loss for the first subnetwork 310 and the second subnetwork 320 according to (i) the predicted data distribution defined by the trained third subnetwork 330, (ii) the first subnetwork output 372, and (iii) the second subnetwork output 374. For example, the dual loss can include a term $\beta \widehat{E_y} E_{X|y}[\log p(X)+\log p(y|X)]$, where $\widehat{E_y} [\bullet]$ indicates an expectation over an empirical data distribution of y (e.g., the empirical data distribution defined by the training data), $E_{X|y}$ indicates an expectation over the predicted data distribution corresponding to the third subnetwork, and $\beta$ is a weight value.

As a particular example, the dual loss can be equal to $$\ell_{dual} = -\left(\underbrace{\hat{E}[\log p(X) + \log p(y|X)]}_{\text{forward direction}} + \right.$$

$$\left. \beta \underbrace{\hat{E}_y E_{X|y}[\log p(X) + \log p(y|X)]}_{\text{dual constraint}} + \underbrace{\hat{E}[\log p(X|y)]}_{\text{backward direction}}\right)$$

The training engine 360 can then determine a parameter update 362 for the first subnetwork 310 and the second subnetwork 330 according to the determined dual loss, e.g., using backpropagation and stochastic gradient descent.

FIG. 4 is a flowchart of an example process 400 for performing retrosynthesis using a neural network. The process 400 can be implemented by one or more computer programs installed on one or more computers and programmed in accordance with this specification. For example, the process 400 can be performed by a retrosynthesis system, e.g., the retrosynthesis system 100 depicted in FIG. 1. For convenience, the process 400 will be described as being performed by a system of one or more computers.

The neural network is configured to generate a prediction of a set of multiple predicted reactants that are combinable to generate a target compound.

The system processes, for each of multiple candidate sets of reactants, a network input characterizing the candidate set using the neural network. This processing includes steps 402, 404, and 406, described in more detail below. That is, the system repeats steps 402-406 for each of the multiple different candidate sets of reactants.

The system processes the network input using a first subnetwork to generate a predicted prior probability of the candidate set of reactants according to an empirical data distribution of sets of predicted reactants and target compounds (step 402).

The system processes the network input using a second subnetwork to generate a predicted conditional probability of the target compound conditioned on the candidate set of reactants according to the empirical data distribution (step 404).

The system processes the network input using a third subnetwork to generate a predicted conditional probability of the candidate set of reactants conditioned on the target compound according to the empirical data distribution (step 406).

The system determines, for each candidate set of the multiple candidate sets of reactants, a score using the generated probabilities (step 408). For example, the system can compute a sum of the logs of the probabilities.

The system selects a particular candidate set of reactants using the determined scores (step 410). For example, the system can select the candidate set with the highest score.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method for generating a prediction of a set of a plurality of predicted reactants that are combinable to generate a target compound, the generating comprising:

processing, for each of a plurality of candidate sets of reactants, a network input characterizing the candidate set using a neural network, the network input being generated from (i) data identifying the target compound and (ii) data identifying the candidate set of reactants, the processing comprising:

processing the network input using a first subnetwork to generate a predicted probability of the candidate set of reactants that represents a likelihood of the candidate set of reactants according to a data distribution of sets of predicted reactants and target compounds;

processing the network input using a second subnetwork to generate a predicted conditional probability of the target compound conditioned on the candidate set of reactants according to the data distribution;

processing the network input using a third subnetwork to generate a predicted conditional probability of the candidate set of reactants conditioned on the target compound according to the data distribution;

determining, for each candidate set of the plurality of candidate sets, a score using the generated probabilities; and selecting a particular candidate set of one or more reactants using the determined scores.

2. The method of claim 1, wherein the score for a particular candidate set is proportional to:

$$\log p(X) + \log p(y|X) + \log p(X|y),$$

wherein X is the candidate set of reactants and y is the target compound.

3. The method of claim 1, wherein the neural network has been trained by:

obtaining a training example characterizing i) a training set of reactants and ii) a training target compound, processing the training example using the neural network, comprising:

processing the training example using the first subnetwork to generate a first subnetwork output, processing the training example using the second subnetwork to generate a second subnetwork output, and processing the training example using the third subnetwork to generate a third subnetwork output corresponding to the third subnetwork, and determining an update to a plurality of parameters of the neural network in order to minimize a dual loss characterizing, for the training set of reactants, a difference between i) a first predicted joint probability of the training set of reactants and the training target compound defined by the first subnetwork output and the second subnetwork output and ii) a second predicted joint probability of the training set of reactants and the training target compound defined by the third subnetwork output.

4. The method of claim 3, wherein the dual loss penalizes a KL divergence between i) a distribution corresponding to the first predicted joint probability and ii) a distribution corresponding to the second predicted joint probability.

5. The method of claim 3, wherein the training comprises:

sampling the training example from an empirical data distribution; and determining the dual loss according to the empirical data distribution.

6. The method of claim 5, wherein the dual loss includes a term $\hat{E}[\log p(X) + \log p(y|X)]$, where $\hat{E}[\bullet]$ indicates an expectation over the empirical data distribution.

7. The method of claim 5, wherein the dual loss includes a term $\hat{E}[\log p(X|y)]$, where $\hat{E}[\bullet]$ indicates an expectation over the empirical data distribution.

8. The method of claim 5, wherein the training comprises:

sampling, from a predicted data distribution corresponding to the third subnetwork, a first example comprising i) a first set of reactants and ii) a first target compound;

processing a first subnetwork input corresponding to the first example using the first subnetwork to generate the first subnetwork output;

processing a second subnetwork input corresponding to the first example using the second subnetwork to generate the second subnetwork output; and determining the dual loss according to the predicted data distribution, the first subnetwork output, and the second subnetwork output.

9. The method of claim 8, wherein the dual loss includes a term $$\beta\hat{E}_y E_{X|y}[\log p(X) + \log p(y|X)]$$

wherein $\hat{E}_y[\bullet]$ indicates an expectation over an empirical data distribution, $E_{X|y}$ indicates an expectation over the predicted data distribution corresponding to the third subnetwork, and $\beta$ is a weight value.

10. The method of claim 1, wherein the first subnetwork is a transformer neural network comprising:

an encoder configured to process a placeholder input and to generate an encoder output; and a decoder configured to process i) the encoder output and ii) an input characterizing a set of reactants to generate the first subnetwork output.

11. The method of claim 1, wherein the second subnetwork is a transformer neural network comprising:

an encoder configured to process an input characterizing a set of reactants and to generate an encoder output; and a decoder configured to process i) the encoder output and ii) an input characterizing the target compound and to generate the second subnetwork output.

12. The method of claim 1, wherein the third subnetwork is a transformer neural network comprising:

an encoder configured to process an input characterizing the target compound and to generate an encoder output; and a decoder configured to process i) the encoder output and ii) an input characterizing a set of reactants and to generate the third subnetwork output.

13. The method of claim 1, further comprising performing in silico screening of a plurality of candidate compounds to select the target compound.

14. The method of claim 1, wherein selecting a particular candidate set of one or more reactants comprises, for each candidate set of the plurality of candidate sets, determining a respective final score using the score corresponding to the candidate set and one or more of:

a number of retrosynthesis steps, a selection of solvents and/or reagents, or a temperature of retrosynthesis.

15. The method of claim 1, further comprising providing data characterizing the particular candidate set of one or more reactants to a robotic synthesis system for synthesizing the target compound.

16. A system comprising one or more computers and one or more storage devices storing instructions that when executed by the one or more computers cause the one or more computers to perform operations for generating a prediction of a set of a plurality of predicted reactants that are combinable to generate a target compound, the generating comprising:

processing, for each of a plurality of candidate sets of reactants, a network input characterizing the candidate set using a neural network, the network input being generated from (i) data identifying the target compound and (ii) data identifying the candidate set of reactants, and the processing comprising:

processing the network input using a first subnetwork to generate a predicted probability of the candidate set of reactants that represents a likelihood of the candidate set of reactants according to a data distribution of sets of predicted reactants and target compounds;

processing the network input using a second subnetwork to generate a predicted conditional probability of the target compound conditioned on the candidate set of reactants according to the data distribution;

processing the network input using a third subnetwork to generate a predicted conditional probability of the candidate set of reactants conditioned on the target compound according to the data distribution;

determining, for each candidate set of the plurality of candidate sets, a score using the generated probabilities; and selecting a particular candidate set of one or more reactants using the determined scores.

17. One or more non-transitory computer-readable storage media storing instructions that when executed by one or more computers cause the one more computers to perform operations for generating a prediction of a set of a plurality of predicted reactants that are combinable to generate a target compound, the generating comprising:

processing, for each of a plurality of candidate sets of reactants, a network input characterizing the candidate set using a neural network, the network input being generated from (i) data identifying the target compound and (ii) data identifying the candidate set of reactants, and the processing comprising:

processing the network input using a first subnetwork to generate a predicted probability of the candidate set of reactants that represents a likelihood of the candidate set of reactants according to a data distribution of sets of predicted reactants and target compounds;

processing the network input using a second subnetwork to generate a predicted conditional probability of the target compound conditioned on the candidate set of reactants according to the data distribution;

processing the network input using a third subnetwork to generate a predicted conditional probability of the candidate set of reactants conditioned on the target compound according to the data distribution;

determining, for each candidate set of the plurality of candidate sets, a score using the generated probabilities; and selecting a particular candidate set of one or more reactants using the determined scores.

18. The system of claim 16, wherein the score for a particular candidate set is proportional to:

$$\log p(X) + \log p(y|X) + \log p(X|y),$$

wherein X is the candidate set of reactants and y is the target compound.

19. The system of claim 16, wherein the neural network has been trained by:

obtaining a training example characterizing i) a training set of reactants and ii) a training target compound, processing the training example using the neural network, comprising:

processing the training example using the first subnetwork to generate a first subnetwork output, processing the training example using the second subnetwork to generate a second subnetwork output, and processing the training example using the third subnetwork to generate a third subnetwork output, and determining an update to a plurality of parameters of the neural network in order to minimize a dual loss characterizing, for the training set of reactants, a difference between i) a first predicted joint probability of the training set of reactants and the training target compound defined by the first subnetwork output and the second subnetwork output and ii) a second predicted joint probability of the training set of reactants and the training target compound defined by the third subnetwork output.

20. The system of claim 19, wherein the dual loss penalizes a KL divergence between i) a distribution corresponding to the first predicted joint probability and ii) a distribution corresponding to the second predicted joint probability.

* * * * *